United States Patent [19]

Fornasier et al.

[11] Patent Number: 4,942,233
[45] Date of Patent: Jul. 17, 1990

[54] THERMOTROPIC DI-S-TRIAZINIC DERIVATIVES

[75] Inventors: Roberto Fornasier; Massimo Tornatore; L. Lowrence Chapoy, all of Novara, Italy

[73] Assignee: Montedison S.p.A., Milan, Italy

[21] Appl. No.: 221,744

[22] Filed: Jul. 20, 1988

[30] Foreign Application Priority Data

Jul. 21, 1987 [IT] Italy ................................ 21369 A/87

[51] Int. Cl.$^5$ .......................................... C07D 403/12
[52] U.S. Cl. .................................................. 544/212
[58] Field of Search ........................................ 544/212

[56] References Cited

PUBLICATIONS

Kleeberg et al., Chemical Abstracts, vol. 83, entry 115796v (1975).

*Primary Examiner*—John M. Ford
*Attorney, Agent, or Firm*—Stevens, Davis, Miller & Mosher

[57] ABSTRACT

Thermotropic di-s-triazinic derivatives are taught having the general formula:

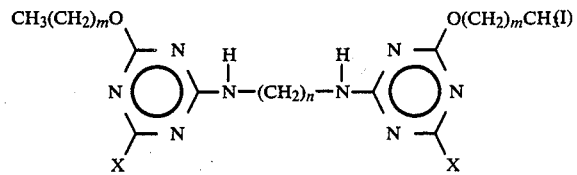

wherein:
m is zero or an integer of from 1 to 5,
n is an integer of from 5 to 30, and
X is a halogen, such as chlorine, or a $CH_3(CH_2)_mO-$ group.

3 Claims, No Drawings

THERMOTROPIC DI-S-TRIAZINIC DERIVATIVES

FIELD OF THE INVENTION

The present invention relates to thermotropic di-s-triazinic derivatives.

BACKGROUND OF THE INVENTION

The chemistry of triazines is a very widely investigated field, because the triazinic derivatives are considerably interesting products. They are widely described in the technical literature because they have many uses, such as, in the agrochemical sector as herbicides, in the field of polymers as additives (for flame-proofing, light-stabilizer purposes, etc.), as monomers for thermoplastic polymers and thermosetting resins, in the field of dyes (reactive dyes for cellulosic fibers), and so forth.

In European patent application No. 53,775, for example, light stabilizers for polyolefins, or for acrylic polymers are disclosed. These are obtained by polycondensation of a diamine with a di-s-triazinic derivative.

This latter product is constituted by two triazinic rings bonded by a diamine and substituted in their 2-position with a halogen and in their 4-position with a group selected from a halogen, or from phenyl, alkoxy, aminic, and so forth radicals.

The present applicant has found now that di-s-triazinic derivatives containing two triazinic rings substituted in their 2- or 4-positions with particular alkoxy groups are optically anisotropic in the molten state, and have liquid crystalline properties.

It is known that the compounds endowed with such properties have in the molten state, and within a well-defined temperature range, an ordered arrangement of molecules. This gives to liquid phase an isotropic properties, which is very interesting.

All the preceding references are hereby incorporated by reference.

SUMMARY OF THE INVENTION

Therefore, an object of the present invention is thermotropic di-s-triazinic derivatives comprising the general formula:

$$CH_3(CH_2)_mO\text{—triazine—}N(H)\text{—}(CH_2)_n\text{—}N(H)\text{—triazine—}O(CH_2)_mCH_3 \quad (I)$$

with X substituents wherein:
m is zero or an integer of from 1 to 5,
n is an integer of from 5 to 30, preferably of from 5 to 12, and
X is a halogen, such as chlorine or a $CH_3(CH_2)_mO$— group.

DETAILED DESCRIPTION OF THE INVENTION

The di-s-triazinic derivatives of the present invention have never been before described in technical literature as compounds having liquid-crystalline properties in the molten state. These products in fact originate an anisotropic molten phase, viz., a mesophase, and have melting temperatures within the range of 50° to 250° C.

The liquid-crystalline organization can be evidenced by means of analyses on Differential Scanning Calorimeter (DSC), analyses on optical microscope under polarized light, and X-ray diffraction.

The thermotropic, or liquid-crystalline, behavior of the di-s-triazinic derivatives of the present invention is not foreseeable on the basis of the teaching of the prior art. See "Electro Optic-Principles and Applications", vol. 38, page 23 (1973); "Applications of Liquid Crystals", Meier (1975).

In fact, the compounds of the present application do not involve any structures of rigid or discoidal shape, or any of the other structure types which are generally assumed as necessary for constituting a mesophase of thermotropic type.

The products having the general formula (I) can be obtained by reacting 2,4-dichloro-6-alkoxy-1,3,5-triazine with an alkylidene-diamine according to the reaction scheme:

$$CH_3(CH_2)_mO\text{—triazine—}X + H_2N\text{—}(CH_2)_n\text{—}NH_2 \longrightarrow$$

(II)  (III)

$$CH_3(CH_2)_mO\text{—triazine—}N(H)\text{—}(CH_2)_n\text{—}N(H)\text{—triazine—}O(CH_2)_mCH_3 + 2HX$$

2,4-dichloro-6-alkoxy-1,3,5-triazine can be obtained by known process, and, in particular, according to the process as disclosed in Journal of American Chemical Society 73, 2986 1951), hereby incorporated by reference.

The reaction is carried out under atmospheric pressure at temperatures within the range of 40° to 100° C. The reaction is preferably, in a solvent having a boiling temperature compatible with the reaction temperature, and having a good solvating power for both the reactants and the products.

Suitable solvents are the polar, aprotic solvents as tetrahydrofuran, dioxane, acetone, methylethylketone, and so forth.

The hydrogen chloride which is formed is neutralized using an organic base in solution or using an inorganic base in suspension. Such bases can be tertiary amines, lutidines, or akali metal hydroxydes, alkali-metal carbonates or bicarbonates wherein the alkali-metal may be sodium, potassium, and so forth.

The reaction product can be recovered from the solution using known methods, such as, by evaporating the solvent, or by precpitating it using a non-solvent, and subsequent filtration to obtain a microcrystalline powder.

Illustrative examples of substituted triazines having the general formula (II), which can be used in the synthesis of the di-s-triazinic derivatives of the present invention, are: 2,4-dichloro-6-methoxy-1,3,5-triazine, 2,4-dichloro-6-ethoxy-1,2,5-triazine, 2,4-dichloro-6-n-propoxy-1,3,5-triazine, and so forth.

Any diamines having the general formula (III) can be used in the synthesis of the di-s-triazines of the present invention. Illustrative examples are: 1,6-diamino-hexane, 1,8-diamino-octane, 1,10-diamino-decane, 1,12-diamino-dodecane, and so forth.

The thermotropic di-s-triazinic derivatives of the present invention can be used as components for optical memory devices. The crystal-liquid crystal and the liquid crystal isotropic melt transistions, even of thermodynamically reversible, can be cinetically controlled by thermal freezing.

This permits the cohexistance and the stability of such phases at room temperature. It is, therefore, possible to easily obtain a thin film with the compound, object of the present invention, in its mesomorphic state and to generate in it, by local heating with a laser beaam isotropic-transparent microzones which are still stable at room temperature. Other uses are as component for opto-electronic displays, as components for nonlinear optics, as additives for thermoplastic polymers, and so forth.

EXAMPLES

For the purpose of better understanding the present invention and to better practicing it, some illustrative nonlimitative examples are reported.

EXAMPLE 1

The preparation is disclosed of N,N'-bis[2-chloro-4-methoxy-1,3,5-triazinyl]-hexamethylene-diamine having the formula:

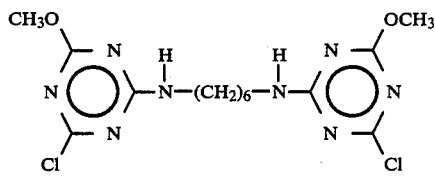

To a flask of 250 ml oaf capacity are charged, 18 g of 2,4-dichloro-6-methoxy-1,3,5-triazine, 6 g of anhydrous sodium carbonate and 80 ml of dioxane. To a dropping funnel are charged, 5.8 g of hexamethylenediamine, 60 ml of dioxane, 20 ml of distilled water.

The diamine-containing solution is added dropwise to the triazine-containing solution. This latter solution is stirred at room temperature. The reaction is continued, always with stirring, at 80° C. for 2 hours.

The solution is then poured into 400 ml of distilled water.

A precipitate is formed which is filtered off, washed with distilled water, and vacuum dried at 60° C.

The product is recrystallized from chloroform.

In this way, after drying at 60° C. under vacuum, 11.22 g (yield: 68%) of product in the form of a white microcrystalline powder is obtained.

The product is identified:
Elemental analysis:
Theoretical: C %: 41.70; H %: 4.96; N %: 27.80; Cl %: 17.60 Found : C %: 41.98; H %: 4.62; N %: 27.88; Cl %: 17.40

Mass Soectrophotometry: $M^+$: 402; 229 187; 173.

The purity of the product is determined by HPLC (High Performance Liquid Chromatrography), and is higher than 95%.

Observations on optical microscope under polarized light evidences the formation of an anisotropic mesophase within the temperature range of from 146° to 150° C.

EXAMPLE 2

The preparation is disclosed of N,N'-bis[2-chloro-4-methoxy-1,3,5-triazinyl]-1,10-diamino-decane having the formula:

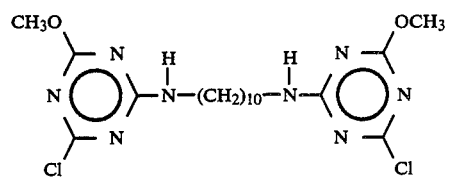

The process is carried out according to the same modalities as in Example 1. However, hexamethylenediamine is replaced by 8.6 g of 1,10-diamino-decane.

After crystallization in chloroform, 14.7 g (yield: 64%) of product in the form of a white microcrystalline powder is obtained.

The product is identified:
Elemental analysis:
Theoretical: C %: 47.07; H %: 6.10; N % : 24.41; Cl %: 15.45 Found: C % :47.39; H %:6.62; N %: 24.30; Cl %: 14.98

Mass Spectrophotometry: $M^+$; 458; 386; 285; 229; 187; 173.

The purity of the product is determined by HPLC, and is higher than 98%.

Observations on optical microscope under polarized light evidences the formation of an anisotropic mesophase within the temperature range of from 112° to 140° C.

EXAMPLES 3-6

By operating with the same modalities as disclosed in Example 1, compounds of general formula (I) are prepared by starting from 2,4-dichloro-6-methoxy-1,3,5-triazine, and from diamines respectively having 7, 8, 9 and 12 carbon atoms.

For such compounds, the following temperature ranges of existence of mesophase (as determined on microscope under polarized light) are observed:

| No. of Diamine Carbon Atoms | Temperature Range of Mesophase Existence (°C.) |
| --- | --- |
| 7 | 132–136 |
| 8 | 113–116 |
| 9 | 91–100 |
| 12 | 81–91 |

EXAMPLE 7

The preparation is disclosed of N,N'-bis[2-chloro-4-methoxy-1,3,5-triazinyl]-1,12-diamino-dodecane having the formula:

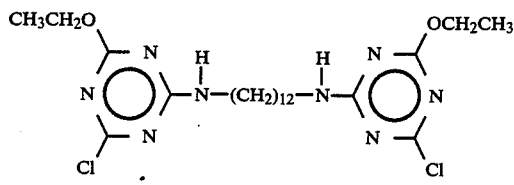

To a flask of 250 ml of capacity are charged, 10 g of diamino-dodecane, 6 g of anhydrous sodium carbonate and 80 ml of dioxane.

To a dropping funnel are charged, 20.8 g of 2,4-dichloro-6ethoxy-1,3,5-triazine and 50 ml of dioxane.

The triazine-containing solution is slowly added dropwise to the diamine-containing solution. This latter solution is kept stirred at room temperature. The reaction is continued, always with stirring, at 50° C. for 1 hour. The solution is then poured into 400 ml of distilled water.

A precipitate is formed which is filtered off, washed with distilled water, dissolved in chloroform, dried with potassium carbonate, filtered, evaporated under vacuum, recrystallized in hexane.

After drying this recrystallized precipitate at 60° C. under vacuum, 14.9 g (yield: 58%) of product in the form of a white microcrystalline powder is obtained. The product is analyzed by:

Elemental analysis:
Theoretical: C %: 51.27; H %: 6.99; N %: 21.75; Cl %: 13.77 Found : C %: 51.11; H %: 7.33; N %: 21.56; Cl %: 13.47

Mass Spectrophotometry: M+: 514; 187; 173.

The observations on optical microscope under polarized light evidence the formation of an anisotropic mesophase within the temperature range o from 79° to 99° C.

Although the invention has been described in conjunction with specific embodiment, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A thermotropic di-s-triazinic derivative of the formula:

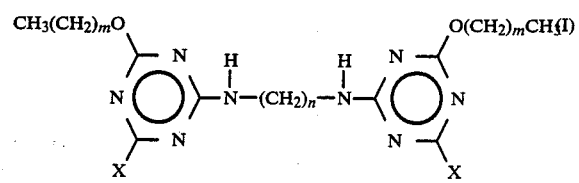

wherein:
m is zero or an integer of from 1 to 5,
n is an integer of from 5 to 30, and
X is a halogen or a $CH_3(CH_2)_mO-$ group.

2. A thermotropic di-s-triazinic derivative according to claim 1, wherein n is an integer within the range of from 5 to 12.

3. A thermotropic di-s-triazinic derivative according to claim 1, wherein X is chlorine.

* * * * *